(12) United States Patent
Williams et al.

(10) Patent No.: US 6,429,177 B1
(45) Date of Patent: Aug. 6, 2002

(54) SEPARATING MULTI-PHASE PERSONAL WASH COMPOSITION IN A TRANSPARENT OR TRANSLUCENT PACKAGE

(75) Inventors: Jason Richard Williams, Berkeley Heights; Ernest Weatherley Macaulay, Morris Township, both of NJ (US); Michael Paul Aronson, West Nyack; Michael Massaro, Congers, both of NY (US); Tom Salmon, Buxtehude (DE)

(73) Assignee: Unilever Home & Personal Care USA, division of Conopco, Inc., Greenwich, CT (US)

( * ) Notice: Subject to any disclaimer, the term of this patent is extended or adjusted under 35 U.S.C. 154(b) by 24 days.

(21) Appl. No.: 09/643,142

(22) Filed: Aug. 22, 2000

(51) Int. Cl.[7] .................................................. A61K 7/00
(52) U.S. Cl. ........................ 510/130; 510/159; 510/417; 510/427; 510/490; 510/508; 510/509
(58) Field of Search ................................ 510/130, 159, 510/426, 417, 427, 473, 490, 508, 509

(56) References Cited

U.S. PATENT DOCUMENTS

| | | | |
|---|---|---|---|
| 3,533,955 A | 10/1970 | Pader | |
| 3,718,609 A | 2/1973 | Weimer | |
| 3,810,478 A | 5/1974 | Olson, Jr. et al. | |

FOREIGN PATENT DOCUMENTS

| | | |
|---|---|---|
| CA | 951213 | 7/1971 |
| EP | 0116422 | 8/1984 |
| EP | 0175485 | 3/1986 |
| GB | 1247189 | 9/1971 |

*Primary Examiner*—Necholus Ogden
(74) *Attorney, Agent, or Firm*—Ronald A. Koatz

(57) ABSTRACT

The invention provides a single chamber transparent or translucent package and personal product composition where when standing, the product forms 2 or more visibly distinct phases and, when agitated, the composition forms a visible single phase.

18 Claims, No Drawings

SEPARATING MULTI-PHASE PERSONAL WASH COMPOSITION IN A TRANSPARENT OR TRANSLUCENT PACKAGE

FIELD OF THE INVENTION

The present invention relates to a cleansing system comprising a transparent or translucent package and an aqueous, personal product multi-phase cleansing composition. Specifically, when left standing, the composition comprises at least two visibly distinct aqueous phases and when agitated, the liquid aqueous phases are dispersible in one another and take on the appearance and lather properties of a conventional liquid personal wash composition (e.g. shower gel). When left to stand, the composition separates into two or more visibly distinct aqueous phases in a maximum period of 24 hours. The compositions of the invention may find application as body wash, shower gel, foam bath or shampoo i.e. as any liquid personal cleansing composition.

BACKGROUND

The use of multiphase liquid cleansers containing water for bath or shower use has been proposed.

It is known, for example, to include a hydrocarbon oil or other oily component which is substantially immiscible with water. Such oily component will form a separate layer after a simple mixture with water is allowed to stand undisturbed.

U.S. Pat. No. 3,718,609 to Weimer, for example, discloses a liquid detergent composition having an aqueous layer and a layer of a liquid, water-immiscible oily material which, when shaken, forms a temporary oil-in-water emulsion (see Abstract).

U.S. Pat. No. 3,810,478 to Olson, Jr. et al. discloses a two-phase shampoo composition made by preparing substantially polar and lipophilic portions of a shampoo composition, and mixing them together.

Two other examples of immiscible liquids are U.S. Pat. No. 3,533,955 to Pader and Canadian Patent No. 951,213.

Each of these is substantially different from the aqueous/aqueous liquids of the invention.

British Patent No. 1,247,189 ('189) (1) discloses compositions for the treatment of fibers containing 0.1 to 80% by wt. detergent, a water-miscible organic solvent and electrolyte; salts of the electrolyte include EDTA which is organic. Mineral salts are precluded because they have a greater tendency to recrystallize leading to product instability. In the present invention, the electrolyte is selected based on solubility to eliminate the problem of recrystallization.

The technology represented by the '189 reference is substantially different than that of the subject invention.

For example, in the subject invention, a certain amount of longer chain polyalkylene ether (e.g., MW 200–6000) or polyether is included.

By contrast, in GB '189 the water miscible organic solvents used are, for example, straight or branch chained monohydric aliphatic alcohols of 1–7 carbons (e.g., ethyl alcohols, isopropyl alcohol) or dihydric alcohols such as hexylene glycol (see column 2, lines 49–68). In short, these are shorter chain solvents which generally are known to be harsh and irritating to the skin. This is not surprising in that the solvents are used in detergent wash compositions compared to the personal product compositions of the invention where milder, longer chain alcohols and/or polyalkylene ethers and/or polyethers are required.

In addition, it is noted that salts used should be organic type salts rather than mineral type (e.g., with solely mineral cations) because the mineral type salts recrystallize and would not form viable liquid compositions. By contrast, electrolytes of the subject invention are selected on the basis of their solubility (soluble enough to form biphasic liquid without recrystallizing out) rather than on basis of being organic or mineral. That is, they theoretically may or may not be organic although mineral salts are more preferred.

EP 0,116,422 (assigned to Reckitt & Coleman) discloses multi-layer liquid compositions in which two liquids are dispersible and which separate on standing. The compositions require sodium hexametaphosphate as detergent builder.

This reference differs from the subject invention in a number of significant ways. First, the "detergent builder" must be sodium hexametaphosphate. This is a not so readily biodegradable chelating/sequestering agent. This is in contrast to the "electrolytes" of the invention which do not function as sequestering agents but are simple salts partitioning primarily into the lower layer and which help ensure the density of the lower layers is greater than that of the upper layers.

Also, to the extent the reference discloses solvents/alcohols, these are used at about 2% weight for weight and are lower MW alcohols typically harsher on skin than higher MW polyalkylene glycols and polyethers found in the subject invention.

Further, to the extent it is not important that the fiber treatment of the reference be shaken as an "experiential" benefit, the reference fails to disclose the composition used in a transparent or translucent container (i.e., using materials having 50% or greater befits, 70% or greater, more preferably 80% or greater light transmittance).

In short, the product of the reference is less environmentally friendly, uses different ingredients and fails to teach or suggest transparent/translucent packaging of the type required for the "experiential" benefits of the product of the subject invention.

EP 0,175,485 (assigned to Reckitt & Coleman) is similar to EP 0,116,422. Again, the compositions require hexametaphosphate and are less environmentally friendly. Also, there is no teaching of the specific polyalkylene glycols /polyethers of the invention and no teaching or suggestion of transparent/translucent containers.

BRIEF DESCRIPTION OF THE INVENTION

Unexpectedly, applicants have found a personal cleansing system comprising a single chamber transparent or translucent package and a personal product composition therein, wherein, when standing, said personal product composition forms two or more visibly distinct aqueous phases and, when agitated, said composition forms a visible single phase product, wherein, when left to stand after said composition has been agitated and has formed a single phase, said composition will again form two or more visibly distinct aqueous phases within 24 hours.

The composition comprises:
a) 5 to 35 wt % of a surfactant selected from the group comprising anionic surfactants, amphoteric surfactants, nonionic surfactants, cationic surfactants and their mixtures
b) 1 to 12 wt % of a thickener
c) 4 to 25 wt % of a polyalkylene glycol, and
d) non-chelating mineral salt selected from the group comprising alkali metal or alkaline earth sulfates, bisulfates, carbonates, bicarbonates, phosphates and their mixtures wherein said non-chelating mineral salt is present in an amount sufficient to induce a separation of said aqueous composition into at least two distinct aqueous layers that are present in a volume ratio of upper to lower phase of from 4:1 to 1:4.

In one embodiment of the invention the composition, when in two phases, comprises:

(1) an upper aqueous layer comprising:
  (a) 5–35% by wt. of total composition (10 to about 75% by wt. upper aqueous phase in part depending on ratio of upper layer to lower layer) of a lathering surfactant selected from the group consisting of anionic surfactants, nonionic surfactants, amphoteric/zwitterionic surfactants, cationic surfactants and mixtures thereof (preferably at least one anionic should be present);
  (b) 4% to 25% by wt. of total composition, preferably 7 to 20% by wt. of a polyalkylene glycol selected from the group consisting of alcohols or polyethers having MW 200 to about 6000
  (c) 1–12% by wt. of total composition, preferably 2 to 10% by wt. of a thickener/viscosity modifier (found substantially totally in the upper layer) to improve the separation of particles and layers on standing; Examples of such thickeners include hydrophobically modified polyethylene glycols, such as PEG (160) sorbitan triisostearate (ex. Kao) or polyol alkoxy ester and laureth 3 (ex Croda)
  (d) less than about 30%, preferably less than 25% of the total non-chelating electrolyte present in the composition (most is in lower layer) such as, for example, salts of sulphate, bisulphate or a carbonate etc. (e.g., magnesium sulphate); and (2) a lower aqueous layer comprising:
  (a) less than 10%, preferably less than 5% of the total surfactant present in the composition of lathering surfactant (greater than 90% and preferably substantially all being found in the upper aqueous layer) as defined in (1)(a) above
  (b) less than 25%, preferably less than 20% of total polyalkylene glycol present in the composition (75% or greater of total polyalkylene glycol being found in upper layer) as in (1)(b) above;
  (c) less than 15%, preferably less than 10% of total thickener present in the composition (greater than 85% and preferably substantially all being found in upper layer) as defined in (1)(c) above; and
  (d) greater than 75%, preferably greater than 85% of the non chelating electrolyte present in the composition as defined in (1)(d) above;
  wherein the viscosity of the lower layer is lower than the viscosity of the upper layer and the viscosity of the total composition after mixing is in range of about 700 to 5000 mPas at shear rate of 10 $s^{-1}$ and 25° C. measured using Haake RV20 Rotovisco Rheometer;
  wherein the viscosity of the mixture is greater than the viscosity of either of the layers alone;
  wherein the density of the lower layer is greater than the density of the upper layer; and
  wherein substantially no recrystallization is visible after the composition has been left standing for 6 months at 0° C. Further, no hydrolysis is readily detectable after 6 months at 45° C.

DETAILED DESCRIPTION OF THE INVENTION

The present invention relates to a cleansing system comprising a single chamber transparent package and a personal product composition therein.

By using a composition which has visible (e.g., transparent or translucent) multi-phases (e.g., biphasic) and can be agitated to provide a single phase prior to use in a single chamber package, the consumer is provided an opportunity to interact with the product and create a positive consumer experience. Further, the final product is a good foaming product which has a lather volume of at least 70 ml., preferably 80–1000 ml. as measured by the pouf method described in the protocol section below. The final product also has a shower-gel like viscosity of 700 to 5000 mPas at a shear rate of 10 $s^{-1}$ at 25° C. as measured by the method noted above.

In an unmixed state, the compositions of the invention will separate into two (or more) stable layers. The upper aqueous layer will comprise (a) surfactant; (b) polyalkylene glycol, and/or polyether to improve mildness and separation; (c) thickener to improve separation at standing; (d) electrolyte (non-chelating); and (e) water. The lower layer will have approximately the same ingredients, but the distribution (i.e., % of total component in upper or lower layer) will be different. It is important to emphasize that at least two of the distinct phases are aqueous solutions and that the composition can be prepared without any oil if desired.

More particularly, the upper layer and the lower layer may be anywhere, respectively, from about an 80:20 ratio to about a 20:80 ratio, preferably 70:30 to 30:70, more preferably 60:40 to 40:60. It should be noted that ratios are not exact and are dependent on composition.

Further, the breakdown of components into upper and lower layers can be approximated as follows:

|  | Upper Layer | Lower Layer |
| --- | --- | --- |
| Surfactant | 80% or greater, preferably substantially all | 20% or lower, preferably substantially absent |
| Polyalkylene Glycol | 65% or greater, preferably 70% or greater | 35% or lower, preferably 30% or lower |
| Thickener | 80% or higher, preferably 85% or higher | 20% or lower, preferably 15% or lower, preferably substantially absent |
| Electrolyte | Less than 25%, preferably less than 20% | Greater than 75%, preferably greater than 80% |

Each of these components is described in greater detail below.

Surfactant

The surfactant generally will comprise 5–35% by wt. of the total composition or 10 to 75% by wt. of the upper aqueous layer. Although it is preferred that greater than 90%, preferably greater than 95% and more preferably substantially all surfactant be present in the upper aqueous layer, as noted, some small amount (less than 20%) may be found in the lower aqueous layer.

The surfactant is a surfactant which may be selected from the group consisting of anionic surfactants, nonionic surfactants, amphoteric/zwitterionic surfactants, cationic surfactants and mixtures thereof. Preferably, there will be at least one anionic surfactant.

The surfactant or surfactants will, when combined with water and agitated, generate a foam or lather of greater than 70 mls, preferably 80–1000 mls. as measured by the pouf method described below.

Non-limiting examples of anionic surfactants are disclosed in McCutcheon's *Detergents and Emulsifiers,* North American Edition (1986), published by Allured Publishing Corporation; McCutcheon's *Functional* materials, North Americas Edition (1992), both of which are incorporated by reference into the subject application.

Examples of anionic surfactants include sarcosinates, sulfates, isethionates, taurates, phosphates, lactylates, glutamates and mixtures thereof. Among isethionates are preferred alkoyl isethionates such as sodium cocoyl isethionate, sodium lauroyl isethionate and mixtures.

The alkyl and alkyl ether sulfates typically have the respective formulae $ROSO_3M$ and $RO(C_2H_4O)_xSO_3M$, wherein R is alkyl or alkenyl of from about 10 to about 30 carbon atoms, x is from about 1 to about 10, and M is a water-soluble cation such as ammonium, sodium, potassium, magnesium and triethanolamine. Another suitable class of anionic surfactants are the water-soluble salts of the organic, sulfuric acid reaction products of the general formula:

$$R_1-SO_3-M$$

wherein $R_1$ is chosen form the group consisting of a straight or branched chain, saturated aliphatic hydrocarbon of radical having from about 8 to about 24, preferably about 10 to about 16, carbon atoms; and M is a cation. Still other anionic synthetic surfactants include the class designated as succinamates, olefin sulfonates having about 12 to about 24 carbon atoms, and β-alkyloxy alkane sulfonates. Examples of these materials are sodium lauryl sulfate and ammonium lauryl sulfate.

Other anionic materials useful herein are soaps (i.e., alkali metal salts, e.g., sodium or potassium salts or ammonium or triethanolamine salts) of fatty acids, typically having from about 8 to about 24 carbon atoms, preferably from about 10 to about 20 carbon atoms. The fatty acids used in making the soaps can be obtained from natural sources such as, for instance, plant or animal-derived glycerides (e.g., palm oil, coconut oil, soybean oil, castor oil, tallow, lard, etc.). The fatty acids can also be synthetically prepared. Soaps are described in more detail in U.S. Pat. No. 4,557,853.

Other useful anionic materials include phosphates such as monoalkyl, dialkyl, and trialkylphosphate salts.

Other anionic materials include alkanoyl sarcosinates corresponding to the formula $RCON(CH_3)CH_2CH_2CO_2M$ wherein R is alkyl or alkenyl of about 10 to about 20 carbon atoms, and M is a water-soluble cation such as ammonium, sodium, potassium and alkanolamine (e.g., triethanolamine), a preferred examples of which are sodium lauroyl sarcosinate, sodium cocoyl sarcosinate, ammonium lauroyl sarcosinate, and sodium myristoyl sarcosinate. TEA salts of sarcosinates are also useful.

Also useful are taurates which are based on taurine, which is also known as 2-aminoethanesulfonic acid. Especially useful are taurates having carbon chains between $C_8$ and $C_{16}$. Examples of taurates include N-alkyltaurines such as the one prepared by reacting dodecylamine with sodium isethionate according to the teaching of U.S. Pat. No. 2,658,072 which is incorporated herein by reference in its entirety. Further non-limiting examples include ammonium, sodium, potassium and alkanolamine (e.g., triethanolamine) salts of lauroyl methyl taurate, myristoyl methyl taurate, and cocoyl methyl taurate.

Also useful are lactylates, especially those having carbon chains between $C_8$ and $C_{16}$. Non-limiting examples of lactylates include ammonium, sodium, potassium and alkanolamine (e.g., triethanolamine) salts of lauroyl lactylate, cocoyl lactylate, lauroyl lactylate, and caproyl lactylate.

Also useful herein as anionic surfactants are alkylamino carboxylates such as glutamates, especially those having carbon chains between $C_8$ and $C_{16}$. Non-limiting examples of glutamates include ammonium, sodium, potassium and alkanolamine (e.g., triethanolamine) salts of lauroyl glutamate, myristoyl glutamate, and cocoyl glutamate.

Non-limiting examples of preferred anionic lathering surfactants useful herein include those selected from the group consisting of sodium lauryl sulfate, ammonium lauryl sulfate, ammonium laureth sulfate, sodium laureth sulfate, sodium trideceth sulfate, ammonium cetyl sulfate, sodium cetyl sulfate, ammonium cocoyl isethionate, sodium lauroyl isethionate, sodium lauroyl lactylate, triethanolamine lauroyl lactylate, sodium caproyl lactylate, sodium lauroyl sarcosinate, sodium myristoyl sarcosinate, sodium cocoyl sarcosinate, sodium lauroyl methyl taurate, sodium cocoyl methyl taurate, sodium lauroyl glutamate, sodium myristoyl glutamate, and sodium cocoyl glutamate and mixtures therefor.

Especially preferred for use herein is ammonium lauryl sulfate, ammonium lauryl ether sulfate, sodium lauryl ether sulfate, sodium lauroyl sarcosinate, sodium cocoyl sarcosinate, sodium myristoyl sarcosinate, sodium lauroyl lactate, and triethanolamine lauroyl lactylates.

Nonionic Lathering Surfactants

Non-limiting examples of nonionic lathering surfactants for use in the compositions of the present invention are disclosed in McCutcheon's, *Detergents and Emulsifiers*, North American Edition (1986), published by allured Published Corporation; and McCutcheon's, *Functional materials*, North American Edition (1992); both of which are incorporated by reference herein in their entirety.

Nonionic lathering surfactants useful herein include those selected form the group consisting of alkyl glucosides, alkyl polyglucosides, polyhydroxy fatty acid amides, alkoxylated fatty acid esters, alcohol ethoxylates, lathering sucrose esters, amine oxides, and. mixtures thereof.

Alkyl glucosides and alkylipolyglucosides are useful herein, and can be broadly defined as condensation articles of long chain alcohols, e.g., C8–30 alcohols, with sugars or starches or sugar or starch polymers i.e., glycosides or polyglycosides. These compounds can be represented by the formula $(S)_n-O-R$ wherein S is a sugar moiety such as glucose, fructose, mannose, and galactose; is an integer of from about 1 to about 1000, and R is a C8–30 alkyl group. Examples of long chain alcohols from which the alkyl group can be derived include decyl alcohol, cetyl alcohol, stearyl alcohol, lauryl alcohol, myristyl alcohol, oleyl alcohol and the like. Preferred examples of these surfactants include those wherein S is a glucose moiety, R is a C8–20 alkyl group, and n is an integer of from about 1 to about 9. Commercially available examples of these surfactants include decyl polyglucoside (available as APG 325 CS from Henkel) and lauryl polyglucoside (available as APG 600 CS and 625 CS from Henkel). Also useful are sucrose ester surfactants such as sucrose cocoate and sucrose laurate.

Other useful nonionic surfactants include polyhydroxy fatty acid amide surfactants, more specific examples of which include glucosamides, corresponding to the structural formula:

wherein $R^1$ is H, $C_1$–$C_4$ alkyl, 2-hydroxyethyl, 2-hydroxy-propyl, preferably $C_1$–$C_4$ alkyl, more preferably methyl or ethyl, most preferably methyl; $R^2$ is $C_5$–$C_{31}$ alkyl or alkenyl, preferably $C_7$–$C_{19}$ alkyl or alkenyl, more preferably $C_5$–$C_{17}$ alkyl or alkenyl, most preferably $C_1$–$C_{15}$ alkyl or alkenyl; and Z is a polyhydroxy hydrocarbyl moiety having a linear hydrocarbyl chain with at least 3 hydroxyl directly connected to the chain, or an alkoxylated derivative (preferably ethoxylated or propyxylated) thereof. Z preferably is a sugar moiety selected from the group consisting of glucose, fructose, maltose, lactose, galactose, mannose, xylose, and mixtures thereof. As especially preferred surfactant corresponding to the above structure is coconut alkyl N-methyl glucoside amide (i.e., wherein the $R^2CO$- moiety is derived form coconut oil fatty acids). Processes for making compositions containing polyhydroxy fatty acid amides are disclosed, for example, in GB Patent Specification 809,060, published Feb. 18, 1959, by Thomas Hedley & Co., Ltd.; U.S. Pat. No. 2,965,576, to E. R. Wilson, issued Dec. 20, 1960; U.S. Pat. No. 2,703,798 to A. M. Schwartz, issued Mar. 8, 1955; and U.S. Pat. No. 1,985,424, to Piggott, issued Dec. 25, 1934; which are incorporated herein by reference in their entirety.

Other examples of nonionic surfactants include amine oxides. Amine oxides correspond to the general formula $R_1R_2R_3NO$, wherein $R_1$ contains an alkyl, alkenyl or monohydroxyl alkyl radical of from about 8 to about 18 carbon atoms, from 0 to about 10 ethylene oxide moieties, and from 0 to about 1 glyceryl moiety, and $R_2$ and $R_3$ contain from about 1 to about 3 carbon atoms and from 0 to about 1 hydroxy group, e.g., methyl, ethyl, propyl, hydroxyethyl, or hydroxypropyl radicals. The arrow in the formula is a conventional representation of a semipolar bond. Examples of amine oxides suitable for use in this invention include dimethyldodecylamine oxide, oleyldi(2-hydroxyethyl) amine oxide, dimethyloctylamine oxide, dimethyldecylamine oxide, dimethyl-tetradecylamine oxide, 3,6,9-trioxaheptadecyldiethylamine oxide, di(2-hydroxyethyl)-tetradecylamine oxide, 2-dodecoxyethyldimethylamine oxide, 3-dodecoxy-2-hydroxypropyldi(3-hydroxypropyl) amine oxide, diemethylhexadecyclamine oxide.

Non-limiting examples of preferred nonionic surfactants for use herein are those selected form the group consisting of C8–C14 glucose amides, C8–C14 alkyl polyglucosides, sucrose cocoate, sucrose laurate, lauramine oxide, cocoamine oxide, and mixtures thereof.

Amphoteric Lathering Surfactants

The term "amphoteric lathering surfactant," as used herein, is also intended to encompass zwitterionic surfactants, which are well known to formulators skilled in the art as a subset of amphoteric surfactants.

A wide variety of amphoteric lathering surfactants can be used in the compositions of the present invention. Particularly useful are those which are broadly described as derivatives of aliphatic secondary and tertiary amines, preferably wherein the nitrogen is in a cationic state, in which the aliphatic radicals can be straight or branched chain and wherein one of the radicals contains an ionizable water solubilizing group, e.g., carboxy, sulfonate, sulfate, phosphate, or phosphonate.

Non-limiting examples of amphoteric surfactants useful in the compositions of the present invention are disclosed in McCutcheon's, *Detergents and Emulsifiers,* North American Edition (1986), published by Allured Publishing Corporation; and McCutcheon's, *Functional Materials,* North American Edition (1992); both of which are incorporated by reference herein in their entirety.

Non-limiting examples of amphoteric or zwitterionic surfactants are those selected from the group consisting of betaines, sultaines, hydroxysultaines, alkyliminoacetates, iminodialkanoates, aminoalkanoates, and mixtures thereof.

Examples of betaines include the higher alkyl betaines, such as coco dimethyl carboxymethyl betaine, lauryl dimethyl carboxymethyl betaine, lauryl dimethyl alphacarboxyethyl betaine, cetyl dimethyl carboxymethyl betaine, cetyl dimethyl betaine (available as Lonaine 16SP from Lonza Corp.), lauryl bis-(2-hydroxyethyl) carboxymethyl betaine, oleyl dimethyl gamma-carboxypropyl betaine, lauryl bis-(hydroxypropyl)alpha-carboxyethyl betaine, coco dimethyl sulfopropyl betaine, lauryl dimethyl sulfoethyl betaine, lauryl bis-(2-hydroxyethyl) sulfopropyl betaine, amidobetaines and amidosulfobetaines (wherein the $RCONH(CH_2)3$ radical is attached to the nitrogen atom of the betaine),oleyl betaine (available as amphoteric Velvetex OLB-50 from Henkel), and cocamidopropyl betaine (available as Velvetex BK-35 and BA-35 from Henkel).

Example of sultaines and hydroxysultaines include materials such as cocamidopropyl hydroxysultaine (available as Mirataine CBS from Rhone-Poulenc).

Preferred for use herein are amphoteric surfactants having the following structure:

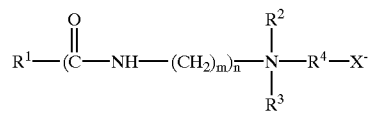

wherein $R^1$ is unsubstituted, saturated or unsaturated, straight or branched chain alkyl having from about 9 to about 22 carbon atoms. Preferred $R^1$ has from about 11 to about 18 carbon atoms; more preferably from about 12 to about 18 carbon atoms; more preferably still from about 14 to about 18 carbon atoms; m is an integer from 1 to about 3, more preferably from about 2 to about 3, and more preferably abort a3; n is either 0 or 1, preferably 1; $R^2$ and $R^3$ are independently selected from the group consisting of alkyl having from 1 to about 3 carbon atoms, unsubstituted or mono-substituted with hydroxy, preferred $R^2$ and $R^3$ are $CH_3$; X is selected form the group consisting of $CO_2$, $SO_3$ and $SO_4$; $R^4$ is selected form the group consisting of saturated or unsaturated, straight or branched chain alkyl, unsubstituted or mono-substituted with hydroxy, having from 1 to about 5 carbon atoms. When X is $CO_2$, $R^4$ preferably has 1 to 3 carbon atoms, more preferably 1 carbon atom. When X is $SO_3$ or $SO_4$, $R^4$ preferably has from about 2 to about 4 carbon atoms, more preferably 3 carbon atoms.

Examples of amphoteric surfactants of the present invention include the following compounds:

Cetyl dimethyl betaine (this material also has the CTFA designation cetyl betaine);

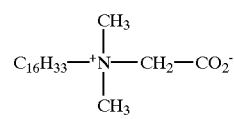

Cocamidopropylbetaine

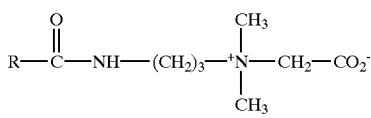

Cocamidopropyl hydroxy sultaine
wherein R has from about 9 to about 13 carbon atoms

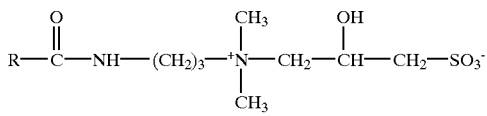

wherein R has from about 9 to about 13 carbon atoms.

Cationic Surfactants

Cationic surfactants are another useful class of surfactants that can be employed as auxiliary agents. They are particularly useful as additives to enhance skin feel, and provide skin conditioning benefits. One class of cationic surfactants is heterocyclic ammonium salts such as cetyl or stearyl pyridinium chloride, alkyl amidoethyl pyrrylinodium methyl sulfate, lapyrium chloride.

Tetra alkyl ammonium salts is another useful class of cationic surfactants. Examples include cetyl or stearyl trimethyl ammonium chloride or bromide; hydrogenated palm or tallow trimethylammonium halides; behenyl trimethyl ammonium halides or methyl sulfates; decyl isononyl dimethyl ammonium halides; ditallow (or distearyl) dimethyl ammonium halides; behenyl dimethy ammonium chloride.

Other types of cationic surfactants that can be employed are the various ethoxylated quaternary amines and ester quats. Examples are PEG-5 stearyl ammonium lactate (e.g., Genamin KSL manufactured by Clarion), PEG-2 coco ammonium chloride, PEG-15 hydrogenated tallow ammonium chloride, PEG 15 stearyl ammonium chloride, dialmitoyl ethyl methyl ammonium chloride, dipalmitoyl hydroxyethyl methyl sulfate, strearyl amidopropyl dimethylamine lactate.

Still other useful cationic surfactants are quaternized hydrolysates of silk, wheat, and keratin proteins.

Polyalkylene Glycol

The polyalkylene glycol generally will comprise 5% to 25% by wt., preferably 7 to 20% by wt. total composition. The polyalkylene glycol will generally divide into at least 65%, preferably 70% of polyalkylene glycol in the upper layer and less than 35%, preferably less than 30% in the lower layer.

Because the compositions of the invention are personal wash compositions primarily intended for contact with skin during wash, the polyalkylene glycol (whose function is to help keep surfactant dissolved in upper aqueous layers, but which may also function as moisturizing benefit agent) should be an alcohol, glycol or polyether of minimal molecular weight which is not irritating to the skin.

Examples of such include alcohols, particularly polyalkylene oxides having MW 200–6000, preferably 200 to 3000. The polyalkylene glycol can be comprised of ethylene oxide, propylene oxide, butylene oxide or their mixtures either as polymers or copolymers. Specific examples include polyethylene glycols such as PEG 400.

Thickeners

The thickeners of the invention will generally comprise 1 to 12%, preferably 2 to 10% by wt. of composition. In one preferred embodiment of the invention, greater than 80%, preferably greater than 85% and most preferably substantially all of the thickeners/viscosity modifier will be found in the upper aqueous layer although 20% or less, preferably 15% or less, preferably 5% or less may be found in lower layer.

The thickener/viscosity modifier serves to thicken the upper layer and maintain separation upon standing.

Thickeners which may be used include hydrophobically modified polyethers. Examples of this class of thickeners which may be used include but are not limited to sugar esters such as PEG (160) sorbitan triisostearate (Rheodol TWS-399C ex Kao Chemicals) or PEG-120 Pentaerythrityl Tetrastearate ex Croda. Other examples include Glucam DOE 120 (PEG 120 Methyl Glucose Dioleate); Rewoderm® (PEG modified glyceryl cocoate, palmate or tallowate) from Rewo Chemicals; Antil® 141 (from Goldschmidt).

Another class of suitable polymers are hydrophobically modified cellulose ethers including but not limited to hydroxyethyl cellulose, hydroxypropylcellulose and cellulose ethers with long pendant chains such as nonoxynyl hydroxyethylcellulose (Amerchol Polymer HM 1500)

Another class of suitable polymers are the hydrophobically modified acrylate copolymers such as Antil 208 ® (ex Goldschmidt) (acrylate/steareth-50 acrylate copolymer).

Another class of suitable polymers are the hydrophobically modified polyurethanes such as Acrysol series (e.g., Acrysol RM-2020) from Rhom and Haas.

Another class of suitable thickeners are xanthan gums, guar gums and chemically modified guar gums.

Electrolyte

The compositions of the invention further comprise less than about 30%, preferably less than 25% of an electrolyte. The electrolyte should preferably not be a chelating electrolyte (which are typically poor in biodegradability). Typically, no more than 25%, preferably 15% or less, more preferably 10% or less of the electrolyte should be in the upper layer while 75% or more, preferably 85% or more should be in the lower layer.

Typically, the electrolyte should be a salt of a sulphate, bisulfate, carbonate, bicarbonate, phosphate, etc. Examples include sodium, potassium sulphate and ammonium sulphate. Magnesium sulphate is particularly preferred.

Aqueous solubility of the salt should exceed 30% wt. to volume at 020 C. such that it may be observed that mineral salts will generally be more preferred than organic salts which typically have much lower solubility.

The compositions of the invention, when unmixed, have a viscosity of the lower layer which is lower than the viscosity of the upper layer and a density of the lower layer which is greater than the density of the upper layer.

The compositions of the invention, in a separated state, are also stable in that no recrystallization (e.g., in the lower layer) occurs even when left sitting for more than 6 months at temperature of 0° C. No hydrolysis is readily detectable after 6 months at 45° C.

Compositions of the invention have an experiential element in that they are intended to be agitated by the consumer to mix and form a single visible phase before separating again after a time, for example, not less than about 15 minutes and not more than about 24 hours.

When mixed, the compositions have a viscosity in the range of 700 to 5000 mPas at a shear rate of $10s^{-1}$ at 25° C., preferably 1000–3000 mPas at a shear rate of $10s^{-1}$ at 25° C., as measured by using Haake RV20 Rotivisco Rheometer.

Further, the viscosity of the mixture is greater than the viscosity of either of the components (e.g., layers) alone.

Finally, the packages in which the compositions are contained are translucent or transparent. By this is meant that the materials (e.g., plastics) have a light transmittance of greater than 50%, preferably greater than 75%, more preferably greater than 85% as measured at wavelength of 460 nm as determined by standard spectroscopy method. In practical terms the package should be sufficiently transparent to permit the separation of the two or more layers to be visible to the naked eye.

Hydrotropes

In addition to the ingredients noted above, the compositions of the invention may contain hydrotropes including but not limited to short chain monohydric or dihydric alcohols, xylene sulphonate and hexylene glycol whose purpose is to avoid the formation of liquid crystal phases resulting from the separation of the surfactant material into the upper phase hence increasing its apparent concentration.

Optionals

In addition to the ingredients noted above, the compositions of the invention may contain a variety of optional ingredients such as set forth below:

The compositions may comprise benefit agents. Benefit agent may be any material that has potential to provide an effect on, for example, the skin.

The benefit agent may be water insoluble material that can protect, moisturize or condition the skin upon deposition from compositions of invention. These may include silicon oils and gums, fats and oils, waxes, hydrocarbons (e.g., petrolatum), higher fatty acids and esters, vitamins, sunscreens. They may include any of the agents, for example, mentioned at column 8, line 31 to column 9, line 13 of U.S. Pat. No. 5,759,969, hereby incorporated by reference into the subject application.

The benefit agent may also be a water soluble material such as glycerin, enzyme and $\alpha$- or $\beta$-hydroxy acid either alone or entrapped in an oily benefit agent.

The benefit agent may be found in either the upper or the lower layer depending on its solubility and partition coefficient, for example, oil may partition into the upper layer while more water soluble agents (e.g., $\alpha$-hydroxyacids) may go into the lower.

The compositions may comprise perfumes, sequestering agents such as EDTA EHDP in amounts 0.01 to 1%, preferably 0.01 to 0.05%; coloring agents, opacifiers and pearlizers such as zinc stearate, magnesium stearate, TiO2, EGMS (ethylene glycol monostrearate) or styrene/acrylate copolymers.

The compositions may further comprise antimicrobials such as 2-hydroxy 4,2'4'trichlorodiphenylether (DP300), 3,4,4'-trichlorocarbanilide, essential oils and preservatives such as dimethyl hydantoin (Glydant XL 1000), parabens, sorbic acid etc.

The compositions may also comprise coconut acyl mono or diethanol amides as suds boosters, and strongly ionizing salts such as sodium chloride and sodium sulfate may also be used to advantage.

Antioxidants such as, for example, butylated hydroxytoluene (BHT) may be used advantageously in amounts of about 0.01% or higher if appropriate.

Cationic conditioners which may be used including Quatrisoft LM-200 Polyquaternium-24, Merquat Plus 3330-Polyquaternium 39; and Jaguar® type conditioners.

Except in the operating and comparative examples, or where otherwise explicitly indicated, all numbers in this description indicating amounts or ratios of materials or conditions or reaction, physical properties of materials and/ or use are to be understood as modified by the word "about".

Where used in the specification, the term "comprising" is intended to include the presence of stated features, integers, steps, components, but not to preclude the presence or addition of one or more features, integers, steps, components or groups thereof.

The following examples are intended to further illustrate the invention and are not intended to limit the invention in any way.

Unless indicated otherwise, all percentages are intended to be percentages by weight.

Methodology

"Pouf Method" Lather Volume Measurement

Lather volume was measured using a pouf method. Lather was generated by dispensing 1 gram of product onto a wet (drained) pouf (mesh sponge), which was then squeezed uniformly for 30 times with one hand. The pouf was gently immersed into water (90° F.) and the generated lather was collected in a graduated tube through a funnel with a big mouth. Its volume was calculated by the difference of the readings between the top and the bottom. The measurement was repeated 7 times for each sample.

By "pouf" is meant a light weight polymeric mesh sponge which can be prepared from readily available raw materials or with specially designed mesh materials. The polymeric mesh sponge is preferably prepared from extruded tubular netting mesh which has been prepared from special strong and flexible polymeric material. Extruded tubular netting mesh of this type, and particularly those prepared from polyethylene, have been used for the covering of meat and poultry and are readily available in industry.

The polymeric mesh sponge comprises a plurality of plys of an extruded tubular netting mesh prepared from a strong flexible polymer, preferably of the group consisting of addition polymers of olefin monomers, and polyamides of polycarboxylic acids and polyamines, said plys of tubular netting mesh are folded upon itself numerous times to form a soft ball-like polymeric mesh sponge.

The tubes or stripes of netted mesh polymer can be securely attached by means of a nylon band or suitable closure. This type of polymeric mesh sponge is disclosed in U.S. Pat. No. 4,462,135, Jul. 31, 1984, to Sanford, incorporated herein by reference.

An example of a hand-held ball-like polymeric mesh sponge is disclosed in U.S. Pat. No. 5,144,744, to Campagnali, Sep. 8, 1992, incorporated herein by reference. It is a diamond-mesh polyethylene sponge obtained from a number of netting tubes stretched over supports, joined and bound together at the center and then released from the supports.

Commercially available "polymeric mesh sponges" are sold by The Body Shop and Bynum Concepts, Inc. Other suppliers include Supremia Use in New Jersey, Sponge Factory Dominicana in the Dominican Republic and Integrated Marketing Group in Harrison, N.Y. Table 1 illustrates some of the components that can be utilized in the present invention.

TABLE 1

Examples of materials that can be employed.

| Ingredient | Function | % W/w |
|---|---|---|
| Sodium Lauryl Ether Sulphate (2 and 3 EO) | Surfactant | 5.00 to 30.00 |
| Triethanolamine Lauryl Ether Sulphate (2 and 3 EO) | Surfactant | 5.00 to 30.00 |
| Magnesium Lauryl Ether | Surfactant | 5.00 to 30.00 |

TABLE 1-continued

Examples of materials that can be employed.

| Ingredient | Function | % W/w |
|---|---|---|
| Sulphate (2 and 3 EO) | | |
| Ammonium Lauryl Ether Sulphate (2 and 3 EO) | Surfactant | 5.00 to 30.00 |
| Potassium Monoalkyl/dialkyl Phosphate | Surfactant | 0.00 to 25.00 |
| Cocoamido Propyl Betaine | Co-surfactant | 0.00 to 32.00 |
| Lauryl Amphoacetate | Co-surfactant | 0.00 to 10.00 |
| Sodium Lauryl Diacetate | Co-surfactant | 0.00 to 10.00 |
| Di Potassium Hydrogen Phosphate | Electrolyte | Up to 30.00 |
| Sulphate (Na, K, $NH_3$ etc . . . ) | Electrolyte | Up to 30.00 |
| Bisulphate (Na, K etc.) | Electrolyte | Up to 30.00 |
| Carbonate (Na, K etc.) | Electrolyte | Up to 30.00 |
| Polyethylene Glycol Av. Mwt. Up to 6000 | Hydrotrope | Up to 40.00 |
| Propan 1-2 Diol | Hydrotrope | 0 to 5 |
| Xylene Sulphonate | Hydrotrope | 0 to 5 |
| Hexylene Glycol | Hydrotrope | 0 to 5 |
| PEG (160) Sorbitan Triisostearate (Rheodol TWS-1399C) | Thickener | 0 to 12.00 |
| Polyol Alkoxyester and Laureth 3 (Crothix) | Thickener | 0 to 12.00 |
| Sodium Chloride | Viscosity modifier | 0 to 1.00 |
| Sunflower Seed Oil | Benefit ingredient/upper phase viscosity and aesthetic modifier | 0 to 10.00 |

EXAMPLE 2

The composition shown in Table 2 was prepared as follows in a single batch process. Polyethylene glycol and surfactant (Sodium lauryl Ether (2 EO) Sulphate) were premixed. Water was slowly added with continuous mixing while heating to about 70° C. Thickener (Polyethylene Glycol (160) Sorbitan Triisostearate) was added and mixed to homogeneous. Electrolyte (Magnesium Sulphate heptahydrate) was added. Mixture was allowed to cool to about 40° C. before addition of perfume and other temperature sensitive ingredients. It is important to mix continuously to prevent premature phase separation before filling.

TABLE 2

Composition of Example 2

| Ingredient | % w/w |
|---|---|
| Sodium lauryl Ether (2 EO) Sulphate | 19.00 |
| Polyethylene Glycol Av. Mwt. 400 | 11.00 |
| Polyethylene Glycol (160) Sorbitan Triisostearate | 4.00 |
| Magnesium Sulphate (hydrated)* | 17.4 |
| Sodium Chloride | 0.25 |
| Perfume | 0.50 |
| Preservative | 0.05 |
| Dye | 0.0002 |
| Distilled Water | 47.8 |

*May be anhydrous, but would lower level of salt and increase level of water.

The density of the composition above is as follows:
Upper phase: 1.0992 g/cm³
Lower phase: 1.2656 g/cm³
Measurement is made using specific gravity bottles.

The compositions shown in Table 3 illustrate the present invention. The compositions were prepared either as described in Example 2 or by a two stage process wherein Polyethylene glycol and surfactant (Sodium lauryl Ether (2 EO) Sulphate) were premixed. Water was slowly added with continuous mixing while heating to about 70° C. Thickener (Polyethylene Glycol (160) Sorbitan Triisostearate) was added and mixed to homogeneous. Mixture was allowed to cool to about 40° C. before addition of perfume and other temperature sensitive ingredients. (Mixture A).

Magnesium sulfate heptahydrate was dissolved in water to yield a concentrated solution (≧40% w/w). (Mixture B) Appropriate quantities of mixtures A and B to provide the final composition of the invention were mixed immediately before filling the final container.

TABLE 3

Further examples of compositions of the invention.

| Ingredient | Example 3 | Example 4 | Example 5 | Example 6 | Example 7 |
|---|---|---|---|---|---|
| Sodium Lauryl Ether Sulphate (2 EO) | 14.0 | — | 16.0 | 15.0 | 15.0 |
| Alpha-olefin sulfonate | — | 15.0 | — | — | — |
| Cocoamidopropylbetaine | 5.0 | — | 3.0 | — | 3.0 |
| Polyethylene glycol (Av MWt. 400) | 11.0 | 10.0 | — | — | 10.0 |
| Polyethylene glycol (Av MWt. 600) | — | — | 11.0 | 7.0 | — |
| Polyethylene glycol (160)Sorbitan Triisostearate | 4.0 | — | 3.0 | 3.0 | — |
| PEG120pentaerythrityl-tetrastearate | — | 3.0 | — | — | 3.8 |
| Sunflower Seed oil | — | — | — | — | 4.0 |
| Cationic guar gum | — | — | — | — | 0.8 |
| Polydimethylsiloxane | — | — | 3.0 | — | — |
| Magnesium Sulfate (hydrated) | 17.4 | — | 17.0 | 24.6 | 16.8 |
| Sodium Carbonate | — | 11.0 | — | — | — |
| Preservative | 0.05 | 0.05 | 0.05 | 0.05 | 0.10 |
| Perfume | 1.0 | 1.0 | 1.0 | 1.0 | 1.25 |
| Propylene Glycol | — | — | — | 3.0 | — |
| Water | 47.55 | 59.95 | 45.95 | 46.95 | 45.25 |

| Ingredient | Example 8 | Example 9 | Example 10 | Example 11 | Example 12 |
|---|---|---|---|---|---|
| Sodium Lauryl Ether Sulphate (2 EO) | 14.0 | 16.0 | 2.0 | 18.5 | 7.5 |
| Sodium cocoyiisethionate | — | — | 5.0 | — | — |
| Cocoamidopropylbetaine | 5.0 | — | 8.0 | — | 3.5 |
| SodiumLauryl amphoacetate | — | 3.0 | — | — | 3.5 |
| Polyethylene glycol (Av MWt. 400) | — | 8.0 | 7.5 | 10.5 | 8.0 |
| Polyethylene glycol (Av MWt. 800) | 9.0 | — | — | — | — |
| Polyethylene glycol (160)Sorbitan Triisostearate | — | 4.0 | — | — | 3.5 |
| PEG200glyceryltallo-wate/PEG7glyceryl-cocoate | 3.5 | — | 3.5 | — | — |
| Hydroxypropylcellulose | — | — | — | 1.2 | — |
| Glycerol | 10.0 | 5.0 | — | 5.0 | 7.5 |
| Polydimethylsiloxane | — | — | 4.0 | — | — |
| Magnesium Sulfate (hydrated) | 18.4 | 19.6 | 15.7 | — | — |
| Ammonium Sulfate | — | — | — | 10.0 | 12.5 |
| Preservative | 0.10 | 0.05 | 0.06 | 0.05 | 0.05 |
| Perfume | 1.25 | 1.0 | 0.95 | 1.0 | 1.0 |
| Isopropylmyristate | — | — | — | — | 3.0 |
| Water | 38.75 | 43.35 | 53.29 | 53.75 | 49.95 |

What is claimed is:
1. A cleansing system comprising a single chamber transparent or translucent package and a personal product composition therein, wherein, when standing, said personal product composition forms two or more visibly distinct aqueous phases and, when agitated, said composition forms a visible single phase product, wherein, when left to stand after said composition has been agitated and has formed a single phase, said composition will again form two or more visibly distinct aqueous phases within 24 hours;

wherein, said composition comprises:
(a) 5 to 35 wt % of surfactant selected from the group comprising anionic surfactants, nonionic surfactants, amphoteric surfactants, cationic surfactants, and mixtures thereof;
(b) 1 to 12 wt % of a thickener;
(c) 4 to 20 wt % of a polyalkylene glycol; and
(d) non-chelating mineral salt selected from the group consisting of alkali metal or alkaline earth sulfates, bisulfates, carbonates, bicarbonates, and mixtures thereof wherein said non-chelating mineral salt is present in an amount sufficient to induce a separation of said aqueous composition into at least two distinct aqueous layers that are present in a volume ratio of upper to lower phase of from 4:1 to 1:4.

2. The composition of claim 1 wherein the polyalkylene glycol (c) is a polyethylene glycol having MW 200 to 6,000 and is present at a level of 6–20 wt %.

3. The composition of claim 1 wherein the thickener (b) is selected from the group consisting of hydrophobically modified polyalkylene glycols, cellulose ethers, hydrophobically modified cellulose ethers, acrylic copolymers and hydrophobically modified polyurethanes.

4. The composition of claim 3 wherein the hydrophobically modified polyalkylene glycol is selected from the group consisting of PEG 160 sorbitan trisostearate, PEG 120 pentaerythrityl tetra stearate and mixtures thereof.

5. The composition of claim 1 wherein the non-chelating mineral salt (d) is magnesium sulfate.

6. The composition of claim 1 wherein one of the anionic surfactants (a) is selected from the group consisting of alkyl ethoxy sulfates, alkyl sulfate, alkoyl isethionates, alpha olefin sulfonates, alkyl carboxylates, alkyl ethoxy carboxylates, and their mixtures.

7. The composition of claim 1 wherein one of the amphoteric surfactants is coco amido propyl betaine.

8. The composition of claim 1 in which the composition additionally contains from 1 to 7 wt % of a hydrotrope selected from the group consisting of xylene sulfonates and low molecular weight mono and dihydric alcohols.

9. A cleansing system comprising a single chamber transparent or translucent package and a personal product composition therein, wherein, when standing, said personal product composition forms two or more visibly distinct aqueous phases and, when agitated, said composition forms a visible single phase product, wherein, when left to stand after said composition has been agitated and has formed a single phase, said composition will again form two or more visibly distinct aqueous phases within 24 hours;

wherein, when in a two-phase mode, said composition comprises:

(1) an upper aqueous layer comprising:
(a) 5 to 35% by wt. of total composition (10 to about 75% by wt. upper aqueous phase of a lathering surfactant selected from the group consisting of anionic surfactant, nonionic surfactant, amphoteric/zwitterionic surfactant, cationic surfactant and mixtures thereof (preferably at least one anionic should be present);
(b) 5% to 20% by wt. total composition is a polyalkylene glycol;
(c) 1 to 2% by wt., of total composition a thickener/viscosity modifier; and;

(2) a lower aqueous layer comprising:
(a) less than 10% of the total surfactant present in the composition of lathering surfactant as defined in (9)(a) above;
(b) less than 25% of total polyalkylene glycol as in (9)(b) above;
(c) less than 15% of total thickener as in (9)(c) above;
(d) non-chelating mineral salt selected from the group comprising alkali metal or alkaline earth sulfates, bisulfates, carbonates, bicarbonates, phosphates and their mixtures wherein said non-chelating mineral salt is present in an amount sufficient to induce a separation of said lower aqueous layer in a volume ratio of upper to lower phase of from 4:1 to 1:4;

wherein the viscosity of the lower layer is lower than the viscosity of the upper layer and the viscosity, after mixing is in the range of about 700 to 5000 mPas at a shear rate of $10s^{-1}$ at 25° C.;

wherein the viscosity of the mixture is greater than the viscosity of either of the layers alone;

wherein the density of the lower layer is greater than the density of the upper layer; and wherein substantially no recrystallization is visible after the composition has been left standing for greater than 6 months at 0° C.; and wherein there is no readily detectable hydrolysis after standing for 6 months at 45° C.

10. A composition according to claim 9, wherein at least one anionic is present as part of surfactant (a).

11. A composition according to claim 9, wherein the polyalkylene glycol (1b) is a polyethylene glycol having a MW 200 to 6,000 and is present at a level of 6–20 wt % of the composition.

12. The composition of claim 9 wherein the thickener (1c) is present in the range of 1–10 wt % and is selected from the group consisting of hydrophobically modified polyalkylene glycols, cellulose ethers, hydrophobically modified cellulose ethers, acrylic copolymers and hydrophobically modified polyurethanes.

13. The composition of claim 12 wherein the hydrophobically modified polyalkylene glycol is selected from the group consisting of PEG 160 sorbitan trisostearate, PEG 120 pentaerythrityl tetra stearate and mixtures thereof.

14. The composition of claim 9 wherein the non-chelating mineral salt (2d) is magnesium sulfate.

15. The composition of claim 9 wherein one of the anionic surfactants (a) is selected from the group consisting of alkyl ethoxy sulfates, alkyl sulfate, alkoyl isethionates, alpha olefin sulfonates, alkyl carboxylates, alkyl ethoxy carboxylates, and their mixtures.

16. The composition of claim 9 wherein one of the amphoteric surfactants (a) is coco amido propyl betaine.

17. The composition of claim 9 in which the composition additionally contains from 1 to 7 wt % of a hydrotrope selected from the group comprising xylene sulfonates, and low molecular weight mono and dihydric alcohols.

18. A composition according to claim 17, wherein the sugar ester is PEG (160) sorbitan triisostearate.

* * * * *